US00PP29721P2

(12) United States Plant Patent
Van Dijk

(10) Patent No.: US PP29,721 P2
(45) Date of Patent: Oct. 2, 2018

(54) ***ANTHURIUM* PLANT NAMED 'ANTHDASZUM'**

(50) Latin Name: ***Anthurium andraeanum* L.**
Varietal Denomination: ANTHDASZUM

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/731,361

(22) Filed: Jun. 1, 2017

(51) Int. Cl.
*A01H 5/02* (2018.01)

(52) U.S. Cl.
USPC ..... Plt./365

(58) Field of Classification Search
USPC ..... Plt./365, 369
CPC ... A01H 5/02; A01H 5/00; A01H 5/12; A01H 6/00
See application file for complete search history.

(56) References Cited

U.S. PATENT DOCUMENTS

PP20,282 P2 * 9/2009 van Dijk ..... A01H 5/02 Plt./369
PP20,283 P2 * 9/2009 van Dijk ..... A01H 5/02 Plt./369
PP28,224 P3 * 7/2017 Van Dijk ..... Plt./369

OTHER PUBLICATIONS

Upov Pluto Plant Variety Database Apr. 28, 2018 for *Anthurium* 'Anthdaszum', retrieved on May 1, 2018, retrieved from the Internet at http://www.upov.int/pluto/en/index.jsp, one page. (Year: 2018).*
EU Community Plant Variety Rights Application No. 2014/2841, Application n°A201405118, filed Nov. 6, 2014, 7 pages.
EU Community Plant Variety Office Official Gazette, Jan. 2015, Feb. 15, 2015, cover page and pp. 29, 52.
EU Community Plant Variety Rights Grant No. Eu 44788, issued Oct. 17, 2016, 2 pages.
EU Community Plant Variety Office Official Gazette, Jun. 2016, Dec. 15, 2016, cover page and p. 73.
Anthura *Anthurium* pot plant catalogue 2017/2018, published May 2017, 2 pages.

* cited by examiner

*Primary Examiner* — June Hwu
(74) *Attorney, Agent, or Firm* — Jondle & Associates, P.C.

(57) ABSTRACT

A new *Anthurium* plant named 'ANTHDASZUM' particularly distinguished by having shiny, bright red, orbicular-cordate and durable spathes that retain the original color for a long period of time, dark green and narrow long-cordate, durable leaves, white spadix with a yellow-orange tip, early and rich flowering continuously throughout the year and a plant height of 40.0 cm to 45.0 cm, is disclosed.

3 Drawing Sheets

Genus and species: *Anthurium andraeanum* L.
Variety denomination: 'ANTHDASZUM'.

BACKGROUND OF THE NEW PLANT

The present invention comprises a new and distinct variety of *Anthurium*, botanically known as *Anthurium andraeanum* L., and hereinafter referred to by the variety name 'ANTHDASZUM'. The new *Anthurium* plant is a product of a planned breeding program conducted by the inventor in Bleiswijk, the Netherlands. The objective of this breeding program was to create a new 40.0 cm to 45.0 cm tall plant, with bright red, orbicular-cordate and durable spathes.

The new variety originated from a cross-pollination made in December 2006 in Bleiswijk, The Netherlands. The female parent was a red *Anthurium* pot plant designated '8477-02' (unpatented), and the male parent was a red *Anthurium* pot plant designated '9863-02' (unpatented).

A single plant was selected from the progeny of the stated cross in June 2008 and has been asexually reproduced repeatedly by tissue culture via shoots in Bleiswijk, The Netherlands over a 6-year period. The present invention has been found to retain its distinctive characteristics through successive asexual propagations.

Plant Breeder's Rights for this variety have been applied for in the European Union on Nov. 6, 2014. 'ANTHDASZUM' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Shiny, bright red, orbicular-cordate spathe;
2) White spadix with yellow-orange tip;
3) Green, narrow, long-cordate leaves; and
4) Red color of the spathe remains for a very long time.

DESCRIPTION OF THE PHOTOGRAPHS

This new *Anthurium* plant is illustrated by the accompanying photographs which show the overall plant habit including blooms, buds and foliage of the plant; the colors shown are as true as can be reasonably obtained by conventional photographic procedures. The photographs are of a 44-week old plant grown in a greenhouse in Bleiswijk, The Netherlands in May 2017. Colors in the photographs may differ from the color values cited in the detailed botanical description, which accurately describe the actual colors of the new variety.

DESCRIPTION OF THE NEW VARIETY

Figure 1:
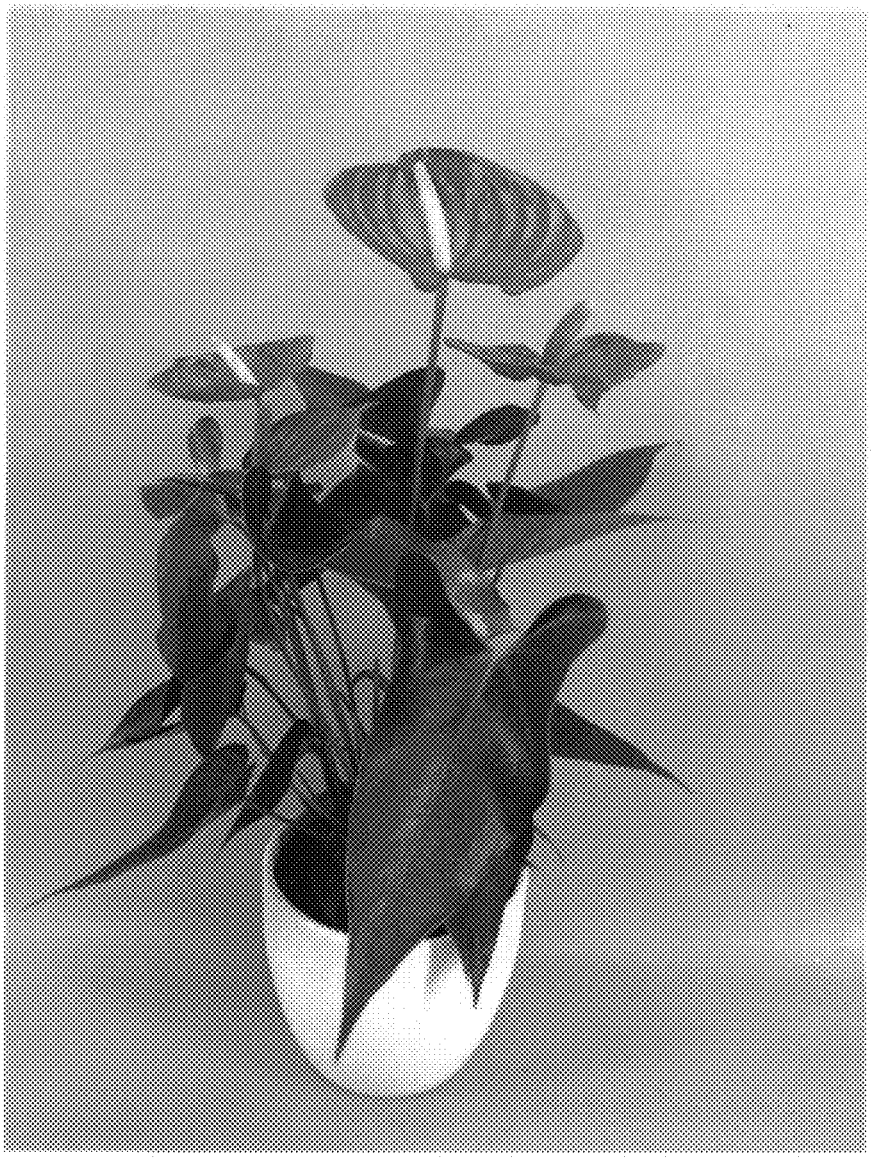
FIG. 1 shows the overall plant habit, including blooms, buds and foliage.
Figure 2:
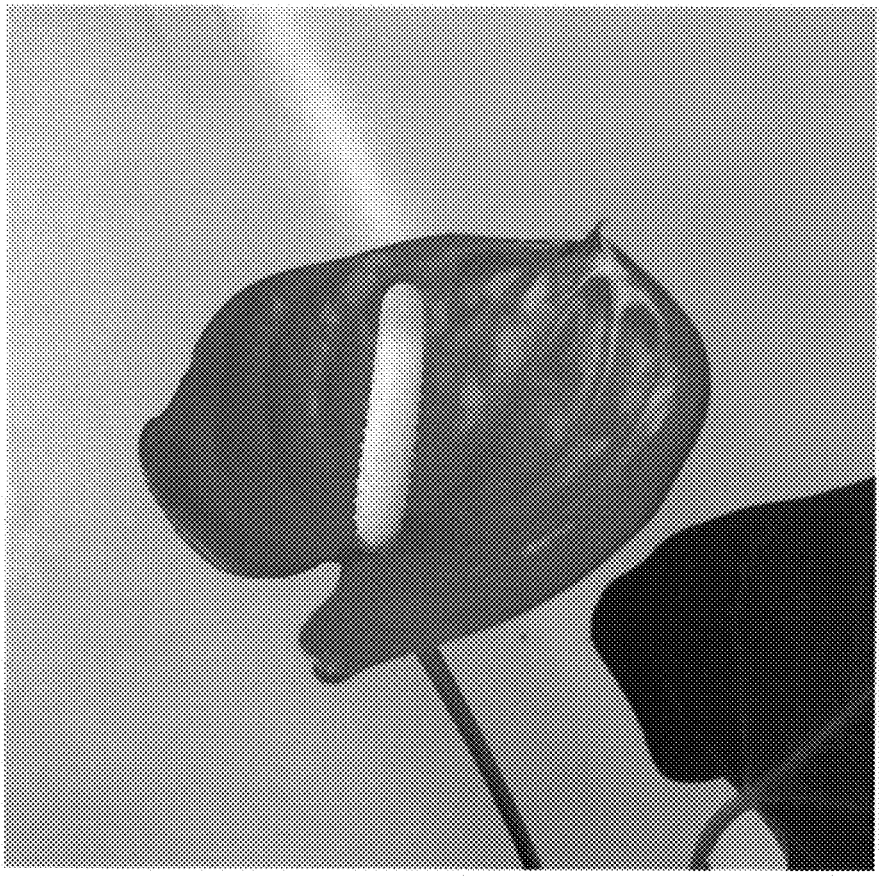
FIG. 2 shows a close-up of the mature spathe.
Figure 3:
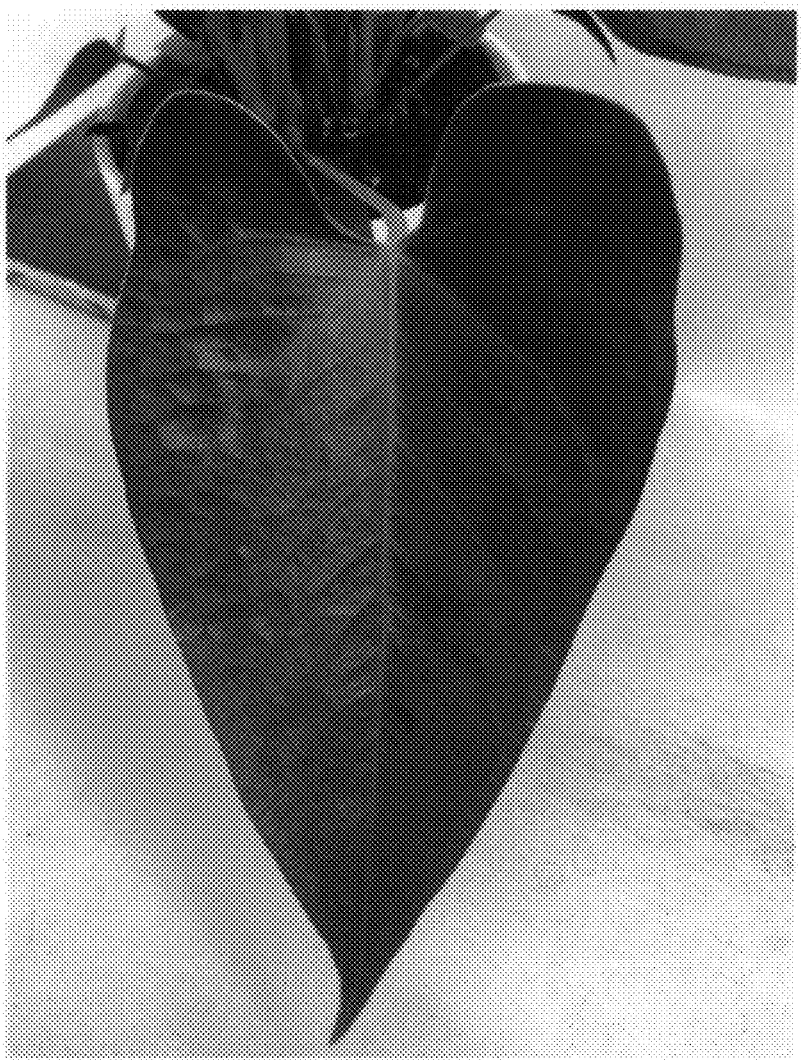
FIG. 3 shows a close-up of the upper leaf blade surface.

The following detailed description sets forth the distinctive characteristics of 'ANTHDASZUM'. The data which define these characteristics were collected from asexual reproductions carried out in Bleiswijk, The Netherlands. The plant history was taken on 42 to 46-week old plants which were planted from tissue culture in 14-centimeter (diameter) pots and grown in a glass greenhouse between 19° C. and 24° C. Observations were made in May 2017. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'ANTHDASZUM'.

Parentage:

*Female parent*.—*Anthurium* plant '8477-02' (unpatented).

*Male parent*.—*Anthurium* plant '9863-02' (unpatented).

Plant:

*Propagation*.—Tissue culture via shoots.

*Root description*.—Fleshy-creamy colored roots with small hairy lateral roots having yellow colored root tips.

*Time to produce a finished flowering plant*.—42 to 46 weeks after planting in a 14 cm (diameter) pot.

*Growth habit*.—Herbaceous perennial.

*Height* (*measured from soil, including inflorescence*).—40.0 cm to 45.0 cm.

*Width* (*measured from leaf tips*).—42.0 cm to 46.0 cm.

Leaves:

*Immature leaves*.—Length: 14.0 cm to 17.0 cm. Width: 8.0 cm to 9.0 cm. Color: Upper surface: RHS 146A. Lower surface: RHS 146B. Texture (both upper and lower surfaces): Shiny.

*Mature leaves*.—Length (fully expanded): 18.0 cm to 21.0 cm. Width: 9.0 cm to 11.0 cm. Shape: Narrow long-cordate. Apex: Acuminate. Base: Cordate. Leaf blade angle with the petiole: Between 120 degrees and 135 degrees. Leaf margin: Entire. Color: Upper surface: RHS 147A. Lower surface: RHS 147B. Texture: Upper surface: Shiny, leathery and thick. Lower surface: Shiny and smooth. Venation: Pinnate veining; the mid-vein and primary veins (the veins that radiate out from the junction of petiole and leaf) protrude at the underside of the leaf blade. Venation color: Upper surface: RHS 146B. Lower surface: RHS 146C.

*Lobes*.—Present. Arrangement: Leaf blade has two lobes extending past the petiole. The lobes are non-touching. Length of lobes of mature leaf blades: 2.5 cm to 3.5 cm. Width of lobes of mature leaf blades: 3.0 cm to 4.0 cm. Distance from petiole/leaf junction to highest point on lobes of mature leaf: 3.0 cm to 4.0 cm.

*Petiole*.—Cross-section: Round. Diameter: 0.3 cm to 0.4 cm. Length: 18.0 cm to 20.0 cm for a mature leaf size. Color: Mature leaf: RHS 144A. Immature leaf: RHS 144B. Cataphyll color surrounding the petiole: Outside: At the base and toward the tip RHS 178C; at the tip RHS 178B. Inside: RHS 181C.

*Geniculum*.—Length: 2.0 cm to 2.5 cm. Width: 0.3 cm to 0.4 cm. Color: RHS 144C.

Inflorescence:

*Arrangement*.—Single.

*Flowering habit* (*length of flowering season*).—Continuous.

*Number of inflorescences per plant*.—5 to 7.

*Fragrance*.—Absent.

*Longevity of inflorescence on plant*.—Half a year.

Spathe:

*Buds*.—The spathe is tightly rolled around the spadix and extrudes from the peduncle sheath. After the spathe is fully open, the peduncle elongates some extra centimeters.

*Arrangement*.—Spathe angle with the peduncle is between 95 degrees and 115 degrees; the spathe stands on a wiry peduncle about 6.0 cm to 9.0 cm above the foliage. The spathe is positioned at the same level to far above the foliage.

*Shape*.—Orbicular-cordate.

*Apex*.—Mucronate.

*Base*.—Cordate.

*Texture*.—Shiny and blistered.

*Margin*.—Entire.

*Size*.—Length: 10.0 cm to 11.0 cm. Width: 9.5 cm to 10.5 cm.

*Lobes*.—Present.

*Arrangement*.—The spathe has two lobes extending past the peduncle. The lobes are non-touching. Length: 1.5 cm to 2.5 cm. Width: 2.5 cm to 3.5 cm.

*Color*.—Just fully open: Upper surface: RHS 45B. Lower surface: RHS 45C. This bright red color remains for a very long period, at least more than 25 weeks after opening.

Peduncle:

*Shape*.—Erect.

*Cross-section*.—Round.

*Length*.—23.0 cm to 26.0 cm.

*Diameter*.—0.25 cm to 0.30 cm.

*Color*.—RHS 144B. Anthocyanin coloration (RHS 180C) appears on the peduncle when the spathe is getting old.

Flowering time:

*General*.—One small rooted untreated tissue culture plant of 8.0 cm tall will flower, depending on season, after 42 to 44 weeks and 5 to 6 blossoms appear. More blossoms appear after some additional weeks so that a full flowering and commercial plant will have 6 to 7 bright red spathes. Smaller blossoms may occur on immature plants.

Spadix:

*Size*.—Length: 4.5 cm to 5.5 cm (depending on flower size). Width (at apex): 0.5 cm to 0.6 cm. Width (at base): 0.7 cm to 0.8 cm.

*Shape*.—Columnar.

*Angle from spadix tip to peduncle*.—140 degrees to 160 degrees.

*Texture*.—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color*.—Immature: RHS 17A. Mature: RHS NN155A. Ages to: RHS 144A.

Flowers:

*Quantity per spadix*.—120 to 150.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 156D.

Reproductive organs:

*Stamens*.—Not visible.

*Pollen amount*.—Absent.

*Pistil*.—Quantity: Many. Length: Less than 0.01 cm. Color: RHS 156D.

*Style*.—Not observed.

*Stigma*.—Shape: Ovoid. Diameter: Less than 0.01 cm. Color: RHS 156D.

*Ovary*.—Rarely visible.

*Ovary color*.—Not measured.

Fruit and seed set: None observed to date.

COMPARISON WITH PARENTAL AND COMMERCIAL VARIETIES

'ANTHDASZUM' differs from the female parent plant '8477-02' (unpatented) in that 'ANTHDASZUM' has orbicular-cordate shaped spathes with mucronate shaped tips, whereas '8477-02' has cordate shaped spathes with abruptly acuminate shaped tips. Additionally, 'ANTHDASZUM' has red-brown cataphyll, whereas '8477-02' has green cataphyll with a touch of moderate red.

ANTHDASZUM' differs from the male parent plant '9863-02' (unpatented) in that 'ANTHDASZUM' has orbicular-cordate shaped spathes with mucronate shaped tips, whereas '9863-02' has cordate shaped spathes with abruptly acuminate shaped tips. Additionally, 'ANTHDASZUM' has red-brown cataphyll, whereas '9863-02' has green cataphyll.

'ANTHDASZUM' differs from similar commercial variety 'ANTHOLYL' (U.S. Plant Pat. No. 20,283) in that 'ANTHDASZUM' has orbicular-cordate shaped spathes, narrow long-cordate leaves and red brown cataphyll, whereas 'ANTHOLYL' has oblong-cordate shaped spathes, elliptical-cordate leaves and green cataphyll. Additionally, 'ANTHDASZUM' has fewer flowers per spadix than 'ANTHOLYL'.

'ANTHDASZUM' differs from similar commercial variety 'ANTHABUDON' (U.S. Plant Pat. No. 20,282) in that 'ANTHDASZUM' has orbicular-cordate shaped spathes and narrow long-cordate leaves, whereas 'ANTHABUDON' has oblong-cordate shaped spathes and elliptical-cordate leaves. Additionally, 'ANTHDASZUM' has fewer flowers per spadix than 'ANTHABUDON'.

'ANTHDASZUM' differs from similar commercial variety 'ANTHDASYM' (U.S. Plant Pat. No. 28,224) in that 'ANTHDASZUM' has a mature spadix color of RHS NN155A and a spathe arrangement that is 6.0 cm to 9.0 cm above the foliage, whereas 'ANTHDASYM' has a mature spadix color of RHS 158B and a spathe arrangement that is 3.0 cm to 5.0 cm above the foliage. Additionally, 'ANTHDASZUM' has a longer spadix and fewer flowers per spadix than 'ANTHDASYM'.

I claim:

1. A new and distinct variety of *Anthurium* plant named 'ANTHDASZUM', substantially as illustrated and described herein.

* * * * *